United States Patent
Okamoto

(10) Patent No.: US 9,086,377 B2
(45) Date of Patent: Jul. 21, 2015

(54) OPTICAL SYSTEM FOR FLUORESCENCE DETECTION AND FINE PARTICLE ANALYZING APPARATUS

(71) Applicant: Sony Corporation, Tokyo (JP)

(72) Inventor: Yoshiki Okamoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 283 days.

(21) Appl. No.: 13/738,581

(22) Filed: Jan. 10, 2013

(65) Prior Publication Data

US 2013/0200272 A1    Aug. 8, 2013

(30) Foreign Application Priority Data

Feb. 7, 2012   (JP) .................. 2012-023854

(51) Int. Cl.
    F21V 9/16     (2006.01)
    G01N 21/64    (2006.01)
    G02B 19/00    (2006.01)

(52) U.S. Cl.
    CPC ............ *G01N 21/6486* (2013.01); *G01N 21/64* (2013.01); *G01N 21/645* (2013.01); *G02B 19/0023* (2013.01); *G02B 19/0076* (2013.01)

(58) Field of Classification Search
    CPC ........................................ G01N 21/64
    USPC ........................................ 250/458.1
    See application file for complete search history.

(56) References Cited

U.S. PATENT DOCUMENTS

| | | | |
|---|---|---|---|
| 2005/0043597 A1* | 2/2005 | Xie | 600/315 |
| 2006/0187499 A1* | 8/2006 | Natori et al. | 358/474 |
| 2009/0091745 A1* | 4/2009 | Levesque et al. | 356/73 |

FOREIGN PATENT DOCUMENTS

| | | |
|---|---|---|
| GB | 01043417 A  * | 9/1966 |
| JP | 2001-509266 | 7/2001 |
| JP | 2002-162350 | 6/2002 |
| JP | 2003-329590 | 11/2003 |
| JP | 2010-099095 | 5/2010 |
| JP | 2011-232259 | 11/2011 |

* cited by examiner

*Primary Examiner* — Christine Sung
(74) *Attorney, Agent, or Firm* — Sony Corporation

(57) ABSTRACT

An optical system for fluorescence detection includes two parabolic mirrors, a first parabolic mirror and a second parabolic mirror, and fluorescent light beams that are incident from different directions are reflected by the first parabolic mirror as parallel light beams to the second parabolic mirror and are converged at one point by the second parabolic mirror.

10 Claims, 6 Drawing Sheets

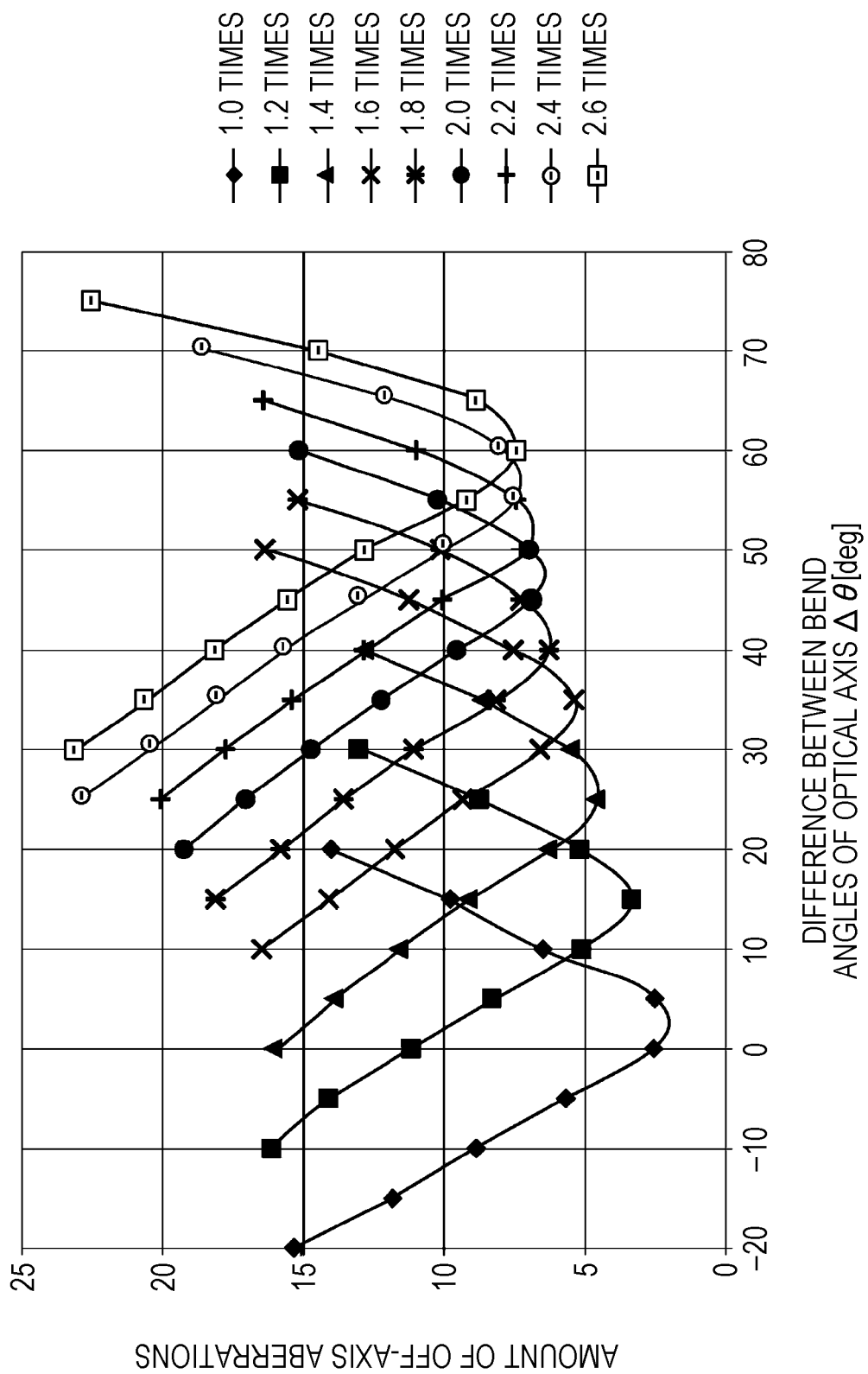

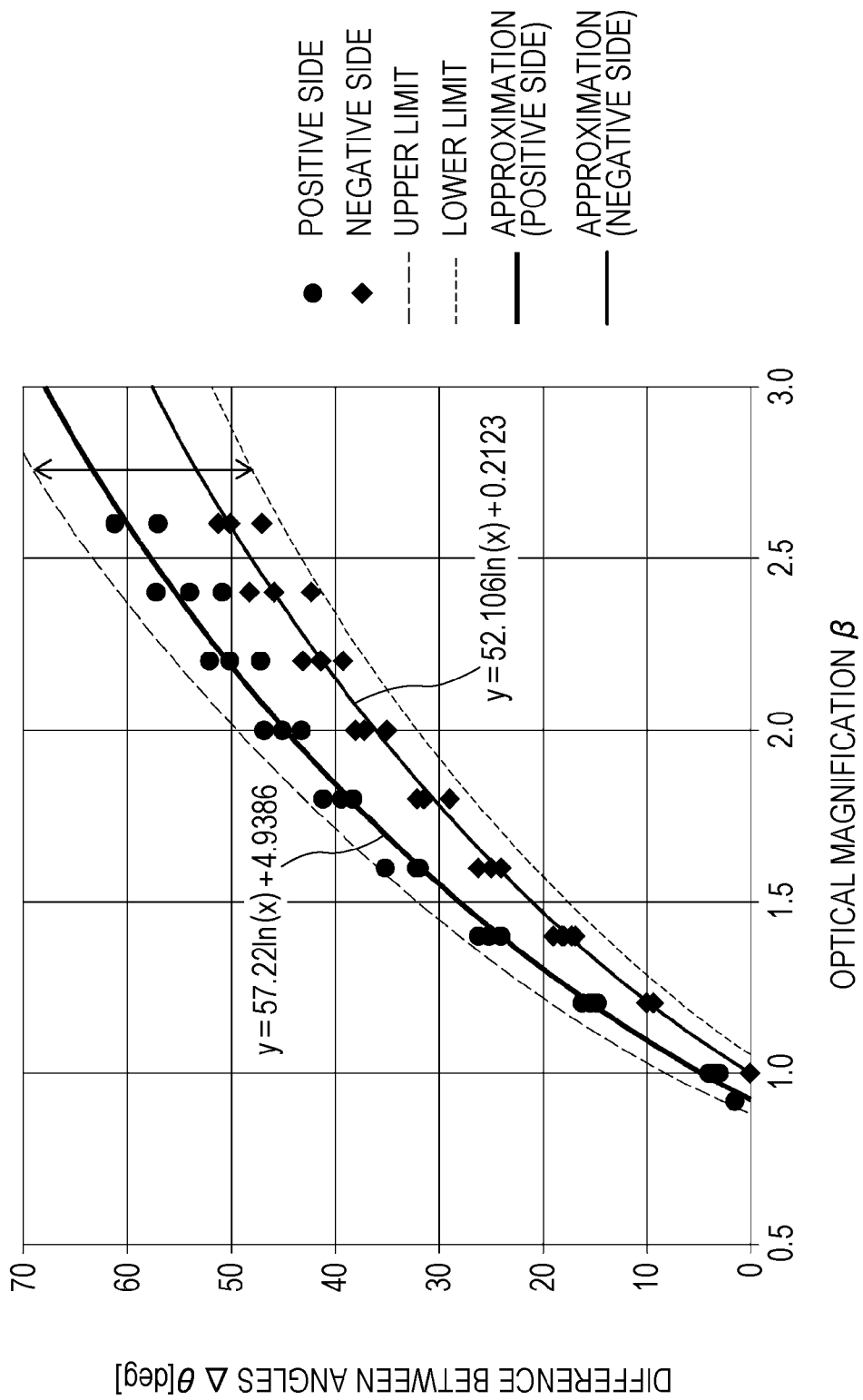

OPTICAL SYSTEM FOR FLUORESCENCE DETECTION AND FINE PARTICLE ANALYZING APPARATUS

CROSS REFERENCES TO RELATED APPLICATIONS

The present application claims priority to Japanese Priority Patent Application JP 2012-023854 filed in the Japan Patent Office on Feb. 7, 2012, the entire content of which is hereby incorporated by reference.

BACKGROUND

The present disclosure relates to optical systems for fluorescence detection and fine particle analyzing apparatuses. In particular, the present disclosure relates to an optical system for detecting a plurality of fluorescent light beams and a fine particle analyzing apparatus that includes the optical system.

In general, an optical measuring method using flow cytometry (a flow cytometer) is utilized when identifying biological fine particles such as cells, microorganisms, liposomes, and the like. Flow cytometry is an analytical method for identifying a plurality of fine particles one by one by irradiating the fine particles, which flow through a flow path in a line, with a laser beam of a specific wavelength and by detecting fluorescent light beams and scattered light beams emitted from each of the fine particles.

In particular, a laminar flow is formed from a sample liquid that includes fine particles, which are to be measured, and a sheath liquid that flows at the periphery of the sample liquid in a flow path in order to arrange the plurality of fine particles included in the sample liquid in a line. When a laser beam is irradiated onto the flow path in this state, the fine particles pass across the laser beam one by one.

In this case, the fluorescent light beams and the scattered light beams emitted from each of the fine particles excited by the laser beam are detected by a light detector such as a charge coupled device (CCD) or a photomultiplier tube (PMT). Then, the light beams detected by the light detector are transformed into electrical signals and converted into numbers. Then, the types, sizes, and structures of the individual fine particles are determined by performing a statistical analysis.

Since fluorescent light beams emitted from biological fine particles such as cells are weak, it is necessary that the fluorescence detection performance of a flow cytometer that analyzes these particles be high. In particular, there is a need to improve the sensitivity of fluorescence detection in multi-beam measurement in which samples are irradiated with a plurality of excitation light beams of different wavelengths, and the resulting plurality of fluorescent light beams are detected.

In the field of light detection, methods for improving detection performance include, for example, a method for detecting fluorescent light beams emitted from samples after amplifying the fluorescent light beams with an optical amplifier (see, Japanese Unexamined Patent Application Publication No. 2010-099095) and a method for electrically correcting a detected signal (see, Japanese Unexamined Patent Application Publication No. 2011-232259). Hitherto, optical systems for light detection using a parabolic mirror or an elliptical mirror as a reflecting mirror have been proposed (see, Japanese Unexamined Patent Application Publication (Translation of PCT Application) No. 2001-509266 and Japanese Unexamined Patent Application Publication Nos. 2003-329590 and 2002-162350 (hereinafter referred to as "Patent Document 3", "Patent Document 4", and "Patent Document 5")).

In the optical systems for light detection of the related art described in Patent Documents 3 and 4, samples are disposed in the vicinity of a focal point of a parabolic mirror, and the parabolic mirror causes light beams emitted from the samples to become parallel light beams, and the parabolic mirror emits the light beams to a detector. In the fluorescence measuring apparatus described in Patent Document 5, fluorescent light beams emitted in various directions from samples are converged on an incidence plane of a detector by a parabolic mirror and an elliptical mirror.

SUMMARY

However, the use of a method for improving the sensitivity of fluorescence detection by providing an optical amplifier or by correcting a detected signal may sometimes amplify a noise component simultaneously; therefore, the method has a limitation with regard to improving the sensitivity of fluorescence detection. It is difficult to apply the technologies described in Patent Documents 3 and 4 to multi-beam measurement, which uses a plurality of light sources, because the parabolic mirrors of the technologies have poor off-axis characteristics. The technology described in Patent Document 5 has a problem that it is not suitable for a back light (a light to be emitted on an excitation light beam side), which is advantageous to obtain fluorescent light beams.

Therefore, it is desirable to provide an optical system for fluorescence detection that can detect fluorescent light beams with a high sensitivity in a measurement using a plurality of light sources and to provide a fine particle analyzing apparatus.

An optical system for fluorescence detection according to the present disclosure includes two parabolic mirrors, a first parabolic mirror and a second parabolic mirror, and fluorescent light beams that are incident from different directions are reflected by the first parabolic mirror as parallel light beams to the second parabolic mirror and are converged at one point by the second parabolic mirror.

In this optical system for fluorescence detection, mirrors having reflecting surfaces whose curvatures are different from each other may be used as the first parabolic mirror and the second parabolic mirror, each of the mirrors having one reflecting surface.

When the ratio of a pseudo focal length $f_2$ of the second parabolic mirror to a pseudo focal length $f_1$ of the first parabolic mirror ($f_2/f_1$) is $\beta$, and the difference between a bend angle $\theta_2$ of an optical axis bent by the second parabolic mirror and a bend angle $\theta_1$ of the optical axis bent by the first parabolic mirror ($\theta_2-\theta_1$) is $\Delta\theta$, these quantities may satisfy the following formula 1:

$$\Delta\theta = a \ln \beta + b \quad (1)$$

where: $49 \leq a \leq 60$, $-2 \leq b \leq 8$

The first parabolic mirror may have a numerical aperture NA of 0.5 or more.

The optical system for fluorescence detection may further include a plane mirror that reflects one of the fluorescent light beams reflected by the first parabolic mirror to the second parabolic mirror.

The first parabolic mirror and the second parabolic mirror may be disposed with a space therebetween.

A fine particle analyzing apparatus according to an embodiment of the present disclosure includes the above-described optical system for fluorescence detection.

The fine particle analyzing apparatus may include two or more light sources and a plurality of light detectors. In such a case, a detection unit in which the light sources emit excitation light beams, and light beams emitted from a fine particle that is irradiated with the excitation light beams are detected by the light detectors may be provided, and the first and second parabolic mirrors may be disposed in the detection unit.

The first and second parabolic mirrors may be disposed between a fine particle that is to be measured and a half mirror that transmits the excitation light beams and reflects fluorescent light beams, and a plurality of fluorescent light beams emitted from the fine particle may be converged on the half mirror.

A plane mirror that reflects fluorescent light beams reflected by the first parabolic mirror to the second parabolic mirror may be provided in the detection unit, so that the fluorescent light beams are reflected on the rear side of the first parabolic mirror by the second parabolic mirror.

The first parabolic mirror and the second parabolic mirror may be disposed with a space therebetween, and the excitation light beams may pass between the first parabolic mirror and the second parabolic mirror so as to be irradiated onto the fine particle.

According to the present disclosure, fluorescent light beams that are incident from different directions are converged at one point by two parabolic mirrors, and thus the fluorescent light beams can be detected with a high sensitivity in a measurement using a plurality of light sources.

Additional features and advantages are described herein, and will be apparent from the following Detailed Description and the figures.

BRIEF DESCRIPTION OF THE FIGURES

FIG. 2 is a graph showing the relationship between a difference $\Delta\theta$ between bend angles of an optical axis and off-axis characteristics (off-axis aberrations) in the case where a bend angle $\theta_1$ of the optical axis at a first parabolic mirror is 70°;

FIG. 3 is a graph showing the relationship between the difference $\Delta\theta$ between the bend angles of the optical axis and the optical magnification $\beta$;

DETAILED DESCRIPTION

Embodiments of the present disclosure will be described in detail with reference to the accompanying drawings. The present disclosure is not limited to the following embodiments. Descriptions will be given in the following order.

1. First Embodiment
(An exemplary optical system for fluorescence detection using two types of parabolic mirrors)
2. Modification of First Embodiment
(An exemplary optical system for fluorescence detection including a plane mirror)
3. Second Embodiment
(An exemplary fine particle analyzing apparatus including the optical system for fluorescence detection according to the first embodiment)

1. First Embodiment

Overall Configuration

Figure 1:
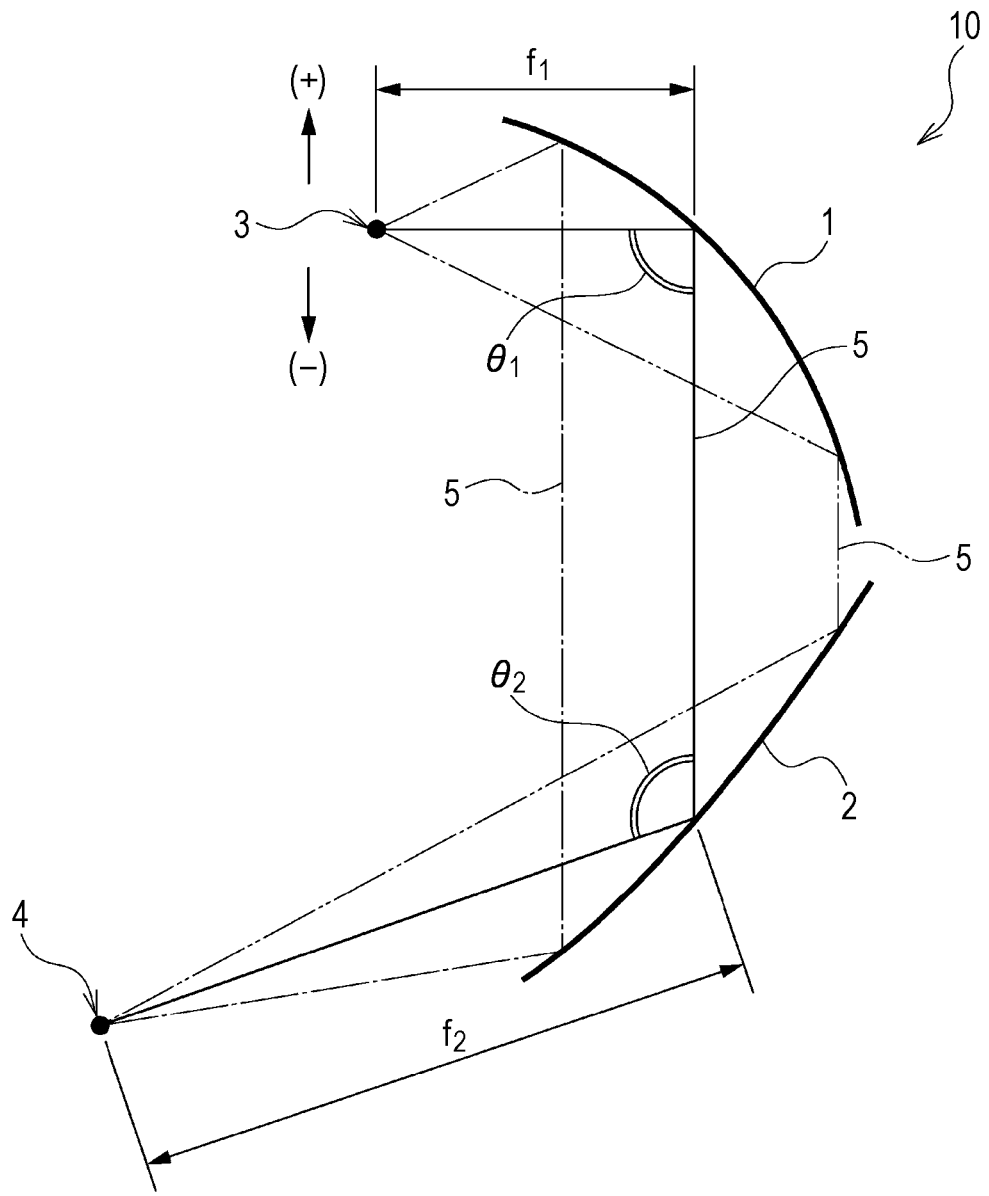
FIG. 1 is a conceptual diagram showing a configuration example of an optical system for fluorescence detection according to a first embodiment of the present disclosure.

An optical system for fluorescence detection according to a first embodiment of the present disclosure will be described below. FIG. 1 is a conceptual diagram showing a configuration example of the optical system for fluorescence detection according to the first embodiment of the present disclosure. As shown in FIG. 1, an optical system 10 according to the present embodiment includes parabolic mirrors 1 and 2 and leads fluorescent light beams 5 that are emitted from samples (an object point 3) to a detection system. In the optical system 10 according to the present embodiment, the fluorescent light beams 5, which are emitted from the samples (the object point 3), are incident from different directions and are reflected by the parabolic mirror 1 as parallel light beams so as to be incident on the parabolic mirror 2. After that, the fluorescent light beams 5 are reflected by the parabolic mirror 2 and converged at one point (an image point 4).

Parabolic Mirrors 1 and 2

The curvatures of reflecting surfaces of the parabolic mirrors 1 and 2 are not particularly limited and may be suitably set according to the optical magnification of the optical system 10. For example, although the parabolic mirror 1 that has a reflecting surface with a large curvature and a short focal length is disposed on the side of the object point 3 in the configuration example shown in FIG. 1, the parabolic mirror 2 that has a reflecting surface with a small curvature and a long focal length may be disposed on the side of the object point 3. In the optical system 10 according to the present embodiment, two parabolic mirrors having reflecting surfaces whose curvatures are the same as each other, and whose focal length are equal to each other may be used, each of the parabolic mirrors having one reflecting surface.

In the optical system 10 according to the present embodiment, for example, when it is necessary to irradiate samples with an excitation light beam, the parabolic mirror 1 and the parabolic mirror 2 may be disposed with a space therebetween so that the excitation light beam passes between the parabolic mirror 1 and the parabolic mirror 2 and will be irradiated onto the sample. As a result, space can be saved. Since the fluorescent light beams 5 between the parabolic mirror 1 and the parabolic mirror 2 take the form of parallel light beams, it is easy to design an optical filter, and the separation performance between the excitation light beam and the fluorescent light beams 5 can be improved. Although a configuration example in which the parabolic mirror 1 and the parabolic mirror 2 are disposed with a space therebetween is shown in FIG. 1, the present disclosure is not limited thereto, and obviously, the parabolic mirror 1 and the parabolic mirror 2 may be disposed without a space therebetween.

Off-Axis Characteristics

In the optical system 10 according to the present embodiment, it is preferable that the relationship between the optical magnification $\beta$ and the difference $\Delta\theta$ between bend angles of the optical axis satisfy the following formula 2. Here, the optical magnification β is the ratio of a pseudo focal length $f_2$ of the parabolic mirror 2 to a pseudo focal length $f_1$ of the parabolic mirror 1 ($f_2/f_1$), and the difference Δθ between the bend angles of the optical axis is the difference between a bend angle $θ_2$ of the optical axis bent by the parabolic mirror 2 and a bend angle $θ_1$ of the optical axis bent by the parabolic mirror 1 ($θ_2-θ_1$):

$$Δθ = a \ln β + b \quad (2)$$

where: 49≤a≤60, −2≤b≤8

FIG. 2 is a graph showing the relationship between the difference Δθ between the bend angles of the optical axis and off-axis characteristics (off-axis aberrations) in the case where the bend angle $θ_1$ of the optical axis at the parabolic mirror 1 is 70°. FIG. 3 is a graph showing the relationship between the difference Δθ between the bend angles of the optical axis and the optical magnification β. As shown in FIG. 2, the difference Δθ between the bend angles of the optical axis at which the amount of off-axis aberrations becomes minimal varies according to the optical magnification β. In other words, when the bend angle $θ_1$ of the optical axis bent by the parabolic mirror 1 is fixed, the bend angle $θ_2$ of the optical axis bent by the parabolic mirror 2 may be changed in accordance with the optical magnification β in order to obtain the best off-axis characteristics.

Since the off-axis characteristics within a surface including an optical axis (a meridional surface) are asymmetrical in the optical system 10 according to the present embodiment, studies were conducted with respect to a positive (+) side and a negative (−) side of the surface. As a result of the studies, as shown in FIG. 3, although there is a small amount of discrepancy on the positive side and the negative side, the quantities can be approximated with the function denoted by the above formula 2 regardless of the bend angle $θ_1$ of optical the axis bent by the parabolic mirror 1. An optical system that has good off-axis characteristics can be provided by adjusting the difference Δθ between the bend angles so as to make a and b shown in the formula 2 be within 49≤a≤60 and −2≤b≤8, respectively.

Numerical Aperture NA

In view of improving detection sensitivity, it is preferable that a parabolic mirror that has a numerical aperture NA of 0.5 or more be used for the parabolic mirror 1, on which the fluorescent light beams 5 emitted from the samples that are incident first. A numerical aperture NA of the parabolic mirror 2 is not particularly limited and can be suitably selected according to the optical magnification that is set or desired.

Operation

The operation of the optical system 10 according to the present embodiment will now be described. In the optical system 10 according to the present embodiment, the fluorescent light beams 5 emitted from the samples (the object point 3) that are incident on the parabolic mirror 1. The fluorescent light beams 5, which are incident on different locations, become parallel light beams that are parallel with one another by being reflected by the parabolic mirror 1 and are incident on the parabolic mirror 2. Then, the parallel light beams will be converged at the same image point 4 by being reflected by the parabolic mirror 2. That is, light beams emitted from samples in different directions can be converged at one point in the optical system 10 according to the present embodiment.

As described in detail above, in the optical system 10 according to the present embodiment, the plurality of fluorescent light beams 5, which are incident on different locations, are converged at one point (the image point 4) by two parabolic mirrors 1 and 2. As a result, the off-axis character-istics and convergent efficiency will be improved, so that the sensitivity for detecting the fluorescent light beams 5 can be improved. The light beams from the parabolic mirror 1 to the parabolic mirror 2 become a parallel light beam flux, and this facilitates the adjustment of the optical axis when assembling a module. As a result, the fluorescent light beams 5 can be detected with a high sensitivity also in multi-beam measurement.

2. Modification of First Embodiment

Figure 4A:
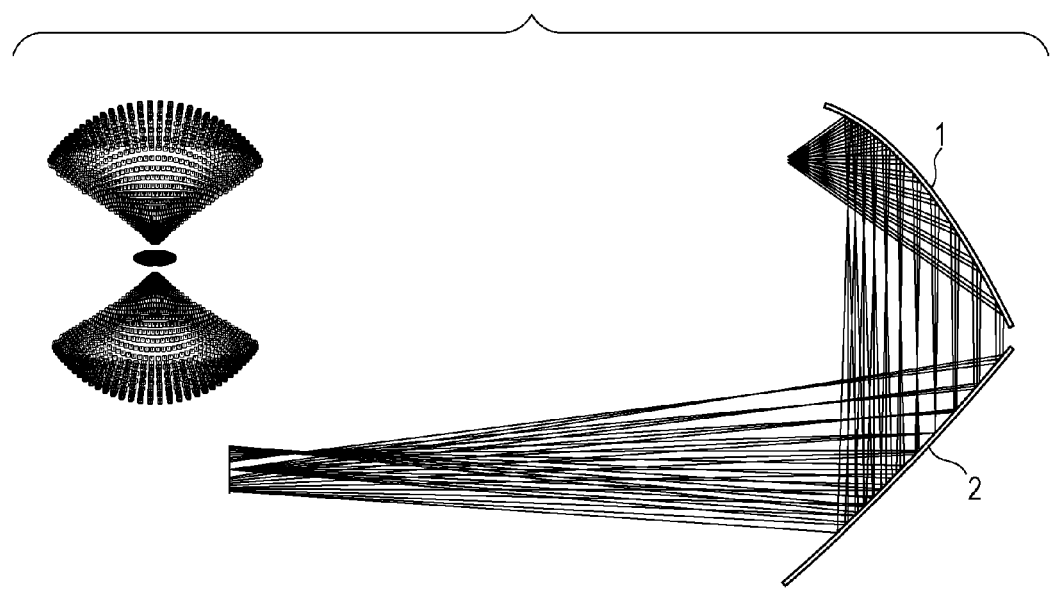
FIG. 4A is a conceptual diagram showing the optical paths and spot size of the optical system illustrated in FIG. 1.
Figure 4B:
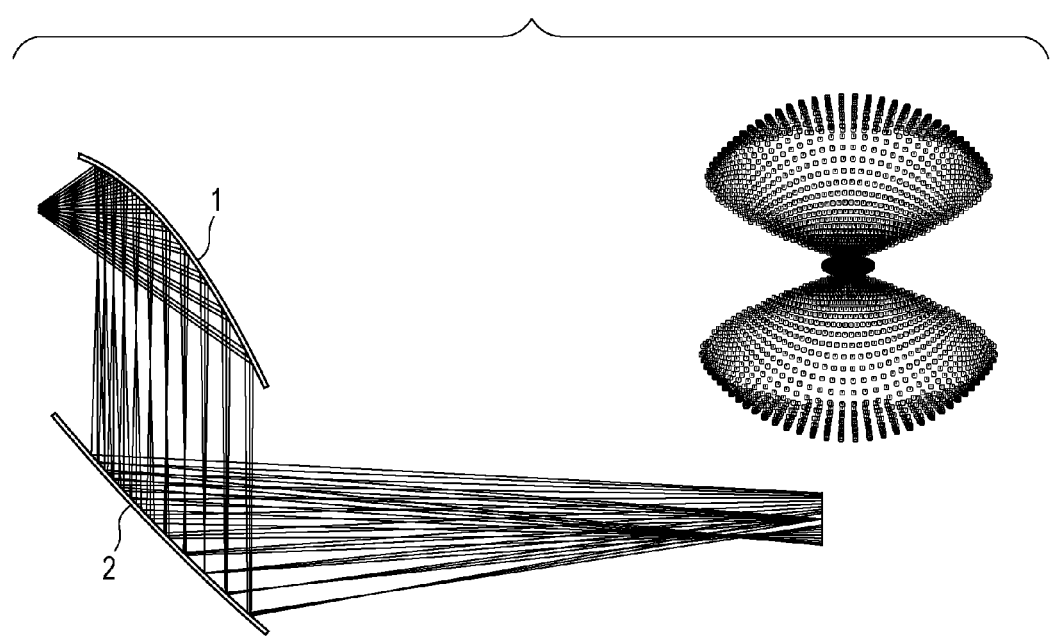
FIG. 4B is a conceptual diagram showing the optical paths and spot size in the case where the orientation of a second parabolic mirror is changed.
Figure 5:
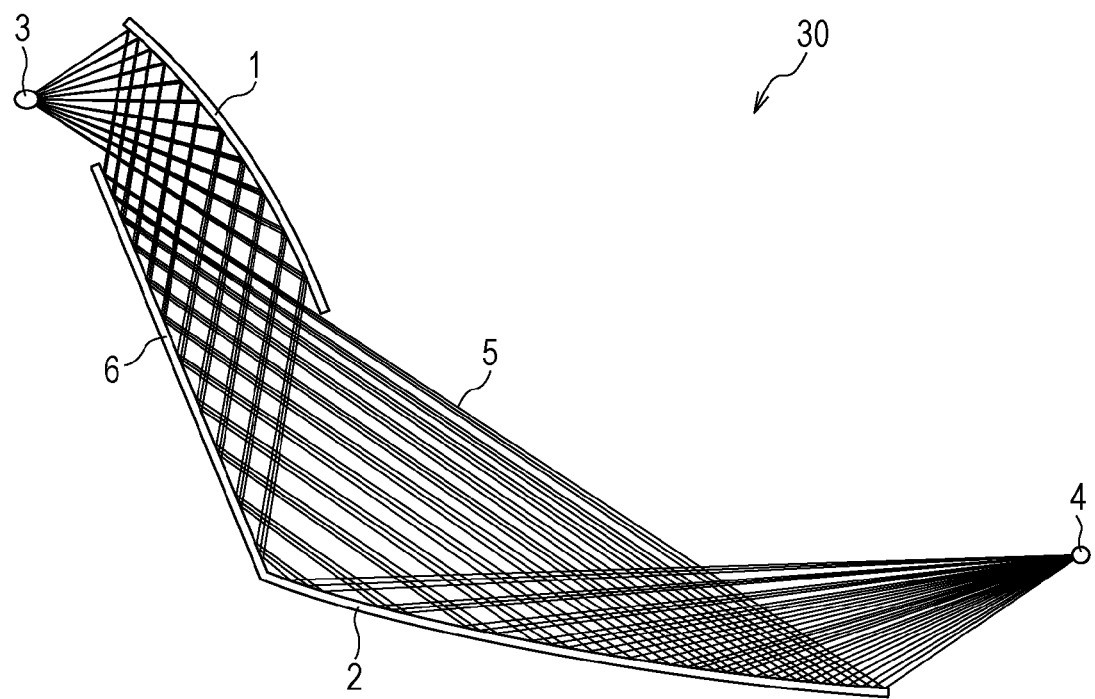
FIG. 5 is a conceptual diagram showing a configuration example of an optical system for fluorescence detection according to a modification of the first embodiment of the present disclosure.

An optical system for fluorescence detection according to a modification of the first embodiment of the present disclosure will now be described. FIG. 4A is a conceptual diagram showing the optical paths and spot size of the optical system 10 illustrated in FIG. 1. FIG. 4B is a conceptual diagram showing the optical paths and spot size when the orientation of the parabolic mirror 2 is changed. FIG. 5 is a conceptual diagram showing a configuration example of the optical system for fluorescence detection according to the present modification. As shown in FIG. 5, in an optical system 30 according to the present modification, a plane mirror 6 that reflects the fluorescent light beams 5 reflected by the parabolic mirror 1 to the parabolic mirror 2 is disposed in addition to the two parabolic mirrors 1 and 2.

In the optical system 10 shown in FIG. 1, the object point 3 and the image point 4 are located on the reflecting surface side of the parabolic mirrors 1 and 2 (in front of the parabolic mirrors 1 and 2), respectively, and the optical paths of the fluorescent light beams 5 are substantially U-shaped. With such a configuration, a system, for example, a flow cytometer, that detects fluorescent light beams from samples that flow through a flow path may sometimes block the flow path. On the other hand, if the parabolic mirror 2 is disposed so that the image point 4 is located on a rear surface side of the parabolic mirror 1 (behind the parabolic mirror 1), and a configuration shown in FIG. 4B in which the optical paths of the fluorescent light beams 5 are substantially Z-shaped is employed, a beam spot will become larger than that and the detection sensitivity will become smaller than that when a configuration shown in FIG. 4A is employed.

Therefore, in the optical system 30 according to the present modification, the plane mirror 6 is disposed between the parabolic mirror 1 and the parabolic mirror 2 so that the fluorescent light beams 5 reflected by the parabolic mirror 1 are incident on the parabolic mirror 2 via the plane mirror 6. This enables the image point 4 to be located on the rear surface side of the parabolic mirror 1 (behind the parabolic mirror 1) without causing the beam spot to become large. As a result, if this configuration is employed in a flow cytometer, the fluorescent light beams 5 can be detected with a high sensitivity without blocking the flow path, and space that the apparatus takes up can be reduced.

If it is necessary to irradiate samples with an excitation light beam in the optical system 30 according to the present modification, for example, a method for providing a hole through which the excitation light beam can pass in the parabolic mirror 1 or the plane mirror 6, or a method for introducing the excitation light beam by placing filters or the like between each mirror or each focal point may be employed. Configuration and advantageous effects of the optical system 30 according to the present modification other than those described above are similar to those of the first embodiment.

3. Second Embodiment

Overall Configuration

A fine particle analyzing apparatus according to a second embodiment of the present disclosure will now be described.

Figure 6:
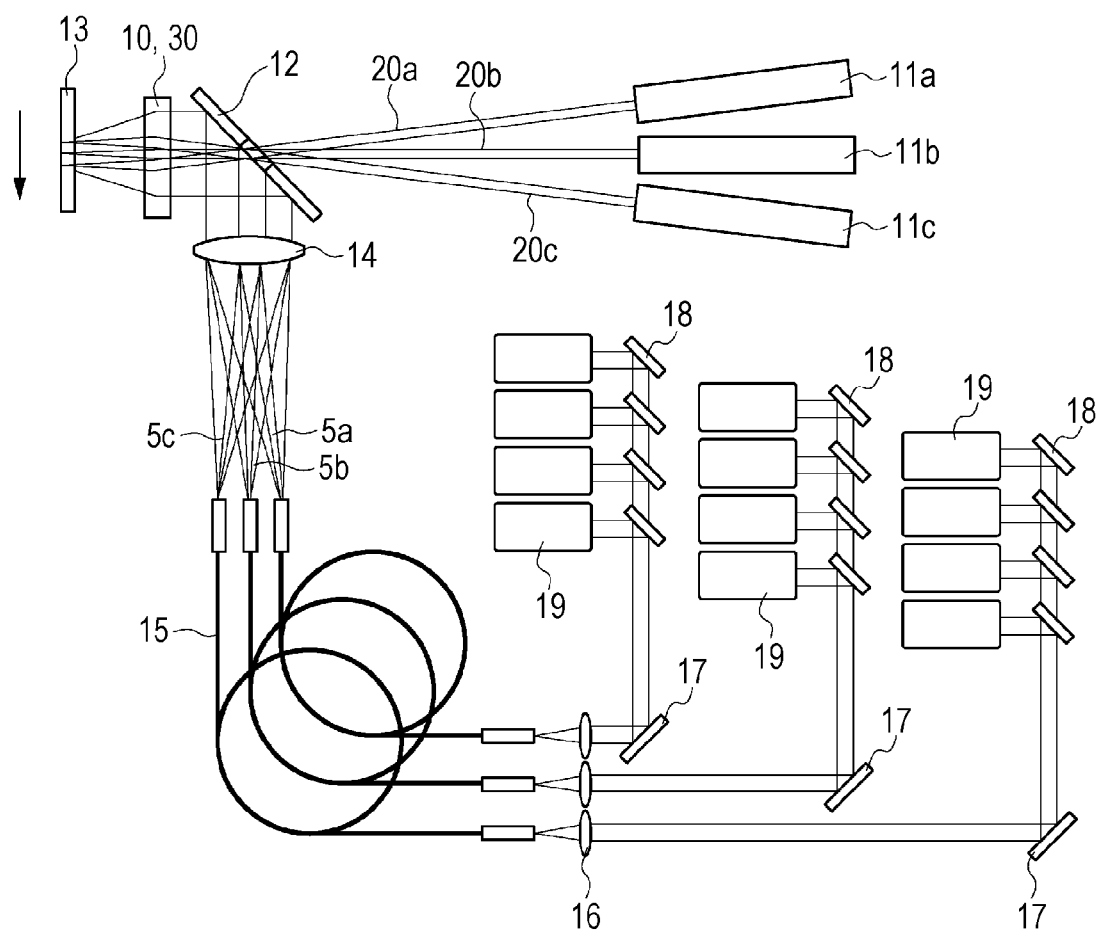
FIG. 6 is a conceptual diagram showing a configuration of a fine particle analyzing apparatus according to a second embodiment of the present disclosure.

FIG. 6 is a conceptual diagram showing a configuration of the fine particle analyzing apparatus according to the present embodiment. The fine particle analyzing apparatus according to the present embodiment includes the optical system 10 according to the first embodiment or the optical system 30 according to the modification of the first embodiment. In the fine particle analyzing apparatus according to the present embodiment, as shown in FIG. 6, at least a plurality of light sources 11*a* to 11*c* and a plurality of light detectors 19 are provided. A multi-beam measurement is performed in the fine particle analyzing apparatus according to the present embodiment. In the multi-beam measurement, a plurality of excitation light beams 20*a* to 20*c* of different wavelengths are irradiated onto samples that flow through a flow path 13, and a resulting plurality of fluorescent light beams 5*a* to 5*c* are detected by the light detectors 19.

Light Sources 11*a* to 11*c*

The light sources 11*a* to 11*c* can be suitably selected according to what is to be measured and the like, and for example, a laser diode, a second harmonic generation (SHG) laser, a gas laser, a high-intensity light emitting diode (LED), or the like may be used as the light sources 11*a* to 11*c*.

Flow Path 13

In the flow path 13 through which the samples flow, a laminar flow is formed from a sample liquid that includes the samples and a sheath liquid that surrounds the periphery of the sample liquid, so that the samples flow through a measurement area which is to be irradiated with the excitation light beams 20*a* to 20*c* in a line. The form of the flow path 13 is not particularly limited, and for example, an analysis chip in which a micro-flow path 13 is formed may be used as the flow path 13.

Detection Unit

A half mirror 12 that transmits the excitation light beams 20*a* to 20*c* and reflects the fluorescent light beams 5*a* to 5*c* is disposed between the flow path 13 and the light sources 11*a* to 11*c*. The optical system for fluorescence detection 10 or 30 is disposed between the half mirror 12 and the flow path 13. In this case, the parabolic mirror 1 and the parabolic mirror 2 of the optical system for fluorescence detection 10 or 30 are disposed with a space therebetween, and the excitation light beams 20*a* to 20*c* pass between the parabolic mirror 1 and the parabolic mirror 2 and are irradiated onto fine particles that flow through the flow path 13.

On the other hand, the plurality of fluorescent light beams 5*a* to 5*c* emitted from the fine particles, which flow through the flow path 13, are reflected by the optical system for fluorescence detection 10 or 30 and converged on the half mirror 12. The apparatus can be reduced in size by employing such a configuration, in which the excitation light beams 20*a* to 20*c* pass through the half mirror 12 and the optical system for fluorescence detection 10 or 30 and are irradiated onto the fine particles.

In the detection unit, for example, optical fibers 15 that lead the fluorescent light beams 5*a* to 5*c* to the light detectors 19, and a fiber coupling lens 14 that converges the fluorescent light beams 5*a* to 5*c* reflected by the half mirror 12 in the optical fibers 15 are provided. In addition, collimator lenses 16, mirrors 17, long-pass filters 18, and the like are provided between the optical fibers 15 and the light detectors 19.

Here, the light detectors 19 are not particularly limited as long as they can detect the fluorescent light beams 5*a* to 5*c* emitted from the sample, and for example, a photodiode (PD), a charge coupled device (CCD), or a photomultiplier tube (PMT), may be used as the light detectors 19. Various optical components can be disposed in a light detection unit as may be necessary.

Operation of Fine Particle Analyzing Apparatus

A method for measuring samples such as fine particles using the fine particle analyzing apparatus according to the present embodiment will now be described. Samples that are to be measured by the fine particle analyzing apparatus according to the present embodiment may be, for example, fine particles such as cells or microbeads, viruses, bacteria, and yeasts, as long as they emit the fluorescent light beams 5*a* to 5*c* by being irradiated with the excitation light beams 20*a* to 20*c*. The samples may be modified with one or more fluorescent dyes.

First, in the fine particle analyzing apparatus according to the present embodiment, the excitation light beams 20*a* to 20*c* are emitted from the light sources 11*a* to 11*c* to the micro-flow path 13. The excitation light beams 20*a* to 20*c* pass through the half mirror 12 and the optical system for fluorescence detection 10 or 30 and are irradiated onto samples (fine particles) that flow through the micro-flow path 13. In this state, the samples, which are to be measured, flow through the micro-flow path 13 in a line, so that the samples can be irradiated with the excitation light beams 20*a* to 20*c* individually.

Therefore, the fluorescent light beams 5*a* to 5*c* that have wavelengths longer than those of the excitation light beams 20*a* to 20*c* are emitted from the samples. The fluorescent light beams 5*a* to 5*c* are converged on the half mirror 12 by the optical system for fluorescence detection 10 or 30 and are introduced in the optical fibers 15 via the fiber coupling lens 14. Then, the fluorescent light beams 5*a* to 5*c* are detected by the light detectors 19 via the collimator lenses 16, the mirrors 17, the long-pass filters 18, and the like.

As described in detail above, the fine particle analyzing apparatus according to the present embodiment includes the optical system 10 according to the above-described first embodiment or the optical system 30 according to the modification of the first embodiment, thereby having good off-axis characteristics. In the fine particle analyzing apparatus according to the present embodiment, fluorescent light beams can be converged at a smaller spot by the optical system for fluorescence detection 10 or 30, so that coupling efficiency when coupling the fluorescent light beams to the optical fibers 15 will be improved. As a result, fluorescent light beams can be detected with a high sensitivity also in multi-beam measurement.

The present disclosure may employ the following configurations.

(1) An optical system for fluorescence detection including:

two parabolic mirrors, a first parabolic mirror and a second parabolic mirror, wherein fluorescent light beams that are incident from different directions are reflected by a first parabolic mirror as parallel light beams to a second parabolic mirror and are converged at one point by the second parabolic mirror.

(2) The optical system for fluorescence detection according to (1), wherein the first parabolic mirror and the second parabolic mirror have reflecting surfaces whose curvatures are different from each other.

(3) The optical system for fluorescence detection according to (1) or (2), wherein when the ratio of a pseudo focal length $f_2$ of the second parabolic mirror to a pseudo focal length $f_1$ of the first parabolic mirror $(f_2/f_1)$ is $\beta$, and the difference between a bend angle $\theta_2$ of an optical axis bent by the second parabolic mirror and a bend angle $\theta_1$ of the optical axis bent by the first parabolic mirror ($\theta_2-\theta_1$) is $\Delta\theta$, these quantities satisfy the following formula (A):

$$\Delta\theta = a \ln \beta + b \quad (A)$$

where: $49 \leq a \leq 60$, $-2 \leq b \leq 8$ (4) The optical system for fluorescence detection according to any one of (1) to (3), wherein the first parabolic mirror has a numerical aperture NA of 0.5 or more.

(5) The optical system for fluorescence detection according to any one of (1) to (4), further including:
a plane mirror that reflects one of the fluorescent light beams reflected by the first parabolic mirror to the second parabolic mirror.

(6) The optical system for fluorescence detection according to any one of (1) to (5),
wherein the first parabolic mirror and the second parabolic mirror are disposed with a space therebetween.

(7) A fine particle analyzing apparatus including:
the optical system for fluorescence detection according to any one of (1) to (6).

(8) The fine particle analyzing apparatus according to (7), further including:
two or more light sources;
a plurality of light detectors; and
a detection unit,
wherein the light sources emit an excitation light beam, and a light beam emitted from a fine particle that is irradiated with the excitation light beam is detected by the light detectors in the detection unit, and
wherein a first parabolic mirror and a second parabolic mirror are disposed in the detection unit.

(9) The fine particle analyzing apparatus according to (8),
wherein a plane mirror that reflects one of the fluorescent light beams reflected by the first parabolic mirror to the second parabolic mirror is disposed in the detection unit, and
wherein the fluorescent light beams is reflected on a rear side of the first parabolic mirror by the second parabolic mirror.

(10) The fine particle analyzing apparatus according to (8) or (9),
wherein the first and second parabolic mirrors are disposed between the fine particle, which is to be measured, and a half mirror that transmits the excitation light beam and reflects a fluorescent light beam, and
wherein a plurality of fluorescent light beams emitted from the fine particle are converged on the half mirror.

(11) The fine particle analyzing apparatus according to any one of (8) or (10),
wherein the first parabolic mirror and the second parabolic mirror are disposed with a space therebetween, and
wherein the excitation light beam passes between the first parabolic mirror and the second parabolic mirror and is irradiated onto the fine particle.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An optical system for fluorescence detection comprising:
two parabolic mirrors, a first parabolic mirror and a second parabolic mirror,
wherein fluorescent light beams that are incident from different directions are reflected by the first parabolic mirror as parallel light beams to the second parabolic mirror and are converged at one point by the second parabolic mirror,
wherein when a ratio of a pseudo focal length $f_2$ of the second parabolic mirror to a pseudo focal length $f_1$ of the first parabolic mirror ($f_2/f_1$) is $\beta$, and a difference between a bend angle $\theta_2$ of an optical axis bent by the second parabolic mirror and a bend angle $\theta_1$ of the optical axis bent by the first parabolic mirror ($\theta_2-\theta_1$) is $\Delta\theta$, these quantities satisfy the following formula:

$$\Delta\theta = a \ln \beta + b$$

where: $49 \leq a \leq 60$, $-2 \leq b \leq 8$.

2. The optical system for fluorescence detection according to claim 1, wherein the first parabolic mirror and the second parabolic mirror have reflecting surfaces whose curvatures are different from each other.

3. The optical system for fluorescence detection according to claim 1, wherein the first parabolic mirror has a numerical aperture NA of 0.5 or more.

4. The optical system for fluorescence detection according to claim 1, further comprising:
a plane mirror that reflects one of the fluorescent light beams reflected by the first parabolic mirror to the second parabolic mirror.

5. The optical system for fluorescence detection according to claim 1, wherein the first parabolic mirror and the second parabolic mirror are disposed with a space therebetween.

6. A fine particle analyzing apparatus comprising:
the optical system for fluorescence detection according to claim 1.

7. The fine particle analyzing apparatus according to claim 6, further comprising:
two or more light sources;
a plurality of light detectors; and
a detection unit,
wherein the two or more light sources emit an excitation light beam, and a light beam emitted from a fine particle that is irradiated with the excitation light beam is detected by one or more of the plurality of light detectors in the detection unit, and
wherein the first parabolic mirror and the second parabolic mirror are disposed in the detection unit.

8. The fine particle analyzing apparatus according to claim 7,
wherein a plane mirror that reflects one of the fluorescent light beam reflected by the first parabolic mirror to the second parabolic mirror is disposed in the detection unit, and
wherein the fluorescent light beam is reflected on a rear side of the first parabolic mirror by the second parabolic mirror.

9. The fine particle analyzing apparatus according to claim 7,
wherein the first and second parabolic mirrors are disposed between the fine particle, which is to be measured, and a half mirror that transmits the excitation light beam and reflects a fluorescent light beam, and
wherein a plurality of fluorescent light beams emitted from the fine particle are converged on the half mirror.

10. The fine particle analyzing apparatus according to claim 7,
wherein the first parabolic mirror and the second parabolic mirror are disposed with a space therebetween, and wherein the excitation light beam passes between the first parabolic mirror and the second parabolic mirror and is irradiated onto the fine particle.

* * * * *